United States Patent [19]

Murtin

[11] 4,288,749

[45] Sep. 8, 1981

[54] METHOD AND APPARATUS FOR MEASURING OXYGEN CONCENTRATION

[75] Inventor: Fernand R. C. Murtin, Paris, France

[73] Assignee: Generale de Fluide, Paris, France

[21] Appl. No.: 33,500

[22] Filed: Apr. 26, 1979

[51] Int. Cl.³ .................................. G01N 27/00
[52] U.S. Cl. .......................................... 324/464
[58] Field of Search ............... 324/465, 464, 470, 459, 324/469; 23/232 E; 422/98

[56] References Cited

U.S. PATENT DOCUMENTS

| | | | |
|---|---|---|---|
| 2,854,625 | 9/1958 | Dudley et al. | 324/464 |
| 3,009,097 | 11/1961 | Strange | 324/468 |
| 3,009,098 | 11/1961 | Simons, Jr. | 324/469 |
| 3,559,049 | 1/1971 | Liebermann et al. | 324/464 |
| 3,820,015 | 6/1974 | Jeunehomme | 324/469 |

Primary Examiner—Eugene La Roche

[57] ABSTRACT

A process for measuring the concentration of oxygen in a gaseous mixture, and particularly for determining the percentage of oxygen in the exhaust gases of an internal or external combustion engine, and ionization probes for the carrying out of this process.

11 Claims, 7 Drawing Figures

METHOD AND APPARATUS FOR MEASURING OXYGEN CONCENTRATION

This invention relates to a process of measuring concentrations of oxygen in a gaseous mixture and in particular in the gases coming from a chemical combustion, such as the exhaust gases of an internal or external combustion engine. The invention also relates to an electric ionization probe which permits the carrying out of the process of the invention and the determination in particular of the percentage of oxygen in the exhaust gases of a combustion engine, a reactor, or a boiler of any type.

In order to determine the oxygen concentration of combustion gases, particularly exhaust gases, there is already known a probe which consists of a closed cylindrical tube containing oxygen or air, which is placed in the path of the gases to be analyzed. This tube is covered on the inside and outside by a layer of zirconium dioxide and a layer of a catalyst, for instance platinum. In this known probe, it has been found that the electromotive force, established in accordance with Arrhenius' law, between two of its faces one of which is in contact with the air and the other with the combustion gases varies as a function of the percentage of oxygen contained in the gases which pass around the probe. The electromotive force supplied by this probe is substantially constant from a percentage of oxygen of zero up to the stoichiometric ratio of the combustion; at that ratio of oxygen, the said electromotive force drops suddenly to a much lower value and remains substantially the same when the percentage of oxygen increases further. Therefore, this known probe can be used with combustion engines to indicate by an "all or nothing" signal, that is to say a logical signal, whether the stoichiometric ratio of the combustion is present or not.

However, this known probe has certain drawbacks. In particular, this probe is sensitive to the action of the lead present in certain fuels, particularly those sold in Europe, the lead attacking the platinum of the catalyst layer.

Furthermore, since this known probe supplies discontinuous information in the vicinity of the stoichiometric ratio stability problems arise in connection with any control system employing this probe as principal actual-value generator.

The said known probe is also sensitive to fouling by heavy hydrocarbons which cause deposits of soot.

There is also known a semi-conductive probe comprising a substrate on which there is deposited a layer of titanium oxide which is made resistive by doping with yttrium. This probe is placed in the path of the gases to be analyzed and is connected, for instance, in one branch of a Wheatstone bridge, whereupon the variation of the resistance of this probe is measured. The variation in conductivity of this probe varies with the diffusion of the oxygen ions in the semi-conductor junction. Up to now, it has not been possible to produce such a semi-conductor probe with a layer of titanium oxide which is sufficiently thin to obtain a sufficiently short response time. Furthermore, such a probe behaves as a thermistor and requires the introduction of temperature compensation. Taking into account the very long response time of this type of probe, of the order of several seconds, it is not possible to use its response signals as principal parameters in a regulating system, for example a system for regulating the richness of the fuel mixture of an internal combustion engine. On the other hand, the mobility of the oxygen ions varies greatly, upon their penetration, with the fouling of the probe, which has the result of substantially modifying the response of the probe.

For further information on these known types of probes reference may be had to the paper of W. J. Fleming "Sensitivity of the Zironia Oxygen Sensor to Temperature and Flow Rate of Exhaust Gas", SAE paper No. 760020 presented in Detroit (USA) in Feb. 1976 at the "International Automotive Engineering Congress and Exposition".

The object of the present invention is a process of measuring the oxygen concentration in a gaseous mixture by utilizing the variation in current resulting from a variation in the initial ionization potential as a function of the oxygen concentration. The utilizing of this physical phenomenon makes it possible, in accordance with the present invention, to determine the concentration of oxygen in a gaseous mixture and in particular in the gases coming from a chemical combustion such as the exhaust gases of an internal or external combustion engine. In accordance with the invention, the gaseous mixture to be analyzed is ionized continuously or by discharge and an electric variable related to the initial ionization potential is measured in the gaseous mixture. The electric variable measured may be the current appearing upon continuous ionization between two electrodes, one of which is subjected to a high voltage or a voltage signal proportional to a high voltage supply.

In a first embodiment of the process of the invention, the same continuous ionization is produced at the same time in a reference gas which is practically at the same temperature as the gaseous mixture to be analyzed, and the ratio of or difference between the currents measured is established in order to obtain therefrom the desired measurement of the oxygen concentration.

In a second embodiment of the process of the invention, on the other hand, ionization by discharge is produced in an ionization cell of the spark-gap type. One can then measure the average value of the current appearing between two electrodes, one of which is subjected to a high voltage. One can also measure the frequency of the electric discharges appearing between these two electrodes.

In all cases one also regulates the high voltage supply of the source electrode in such a manner that the ratio of high voltage to current or the high voltage itself or else the current delivered by the high voltage supply is maintained at a constant value.

In the second embodiment of the process of the invention, the ionization by discharge has the advantage of being particularly significant with respect to the oxygen concentration rate due to the special photoionization characteristics of the oxygen molecules which is superimposed on the electric ionization phenomenon. The effect of variation of the density of the gaseous mixture as a function of its temperature and its pressure which is present, however, remains of the second order and can in general therefore be neglected. However, if one desires to take it into account, it is easy to effect a correction of the measurement since one can easily determine the temperature and the pressure of the gaseous mixture to be analyzed and therefore the correction to be made.

In the event that the process of the invention is applied to the measurement of the concentration of oxygen in gases coming from a chemical combustion such as the exhaust gases of an internal or external combustion engine, it will be noted that strictly speaking the measurement is slightly falsified by the existence of nitrogen oxides in the exhaust gases, they having an initial ionization potential which is less than that of oxygen. Actually, however, the amounts of nitrogen oxide are very definitely less than those of oxygen so that this effect is practically negligible. Furthermore, the amount of nitrogen oxide contained in the exhaust gases decreases with increasing percentages of oxygen. Now for low percentages of oxygen the variation of the initial ionization potential as a function of the oxygen is greater, which increases the precision of the measurement, making negligible the possible influence of these nitrogen oxides in the vicinity of the low percentages of oxygen which are present in the exhaust gases upon normal operation.

Another object of the present invention is an electric probe which makes it possible to carry out the process of the invention and to analyze the gases coming from a chemical combustion and in particular to determine the concentration of oxygen in the exhaust gases of an internal or external combustion engine. The probe of the invention does not have the drawback of the aforementioned known probes, particularly their lack of fidelity and reliability. Furthermore it is relatively inexpensive to manufacture.

In a first embodiment, the electric ionization probe of the present invention comprises a high voltage supply; a first ionization cell comprising a source electrode connected to the supply and a receiving electrode, the said first cell being arranged in the path of the gases to be analyzed; the probe furthermore contains a second ionization cell which is identical to the first cell and the source electrode of which is also connected to the supply and is traversed by ambient air brought practically to the same temperature as the gases passing through the first cell, which air acts as reference gas so as to overcome errors in measurement resulting from the temperature and pressure conditions of the gases to be analyzed. The electric probe of the invention furthermore comprises a processing device which picks up the currents appearing on the receiving electrodes of the two cells. The two ion source electrodes of the two cells can be fed either with a positive high voltage or with a negative high voltage. In accordance with one embodiment of the invention, the probe furthermore has means which make it possible to regulate the high voltage source in such a manner that is supplies a constant voltage or current. In accordance with another embodiment, the regulating means make it possible to regulate the source of high voltage in such a manner that the ratio of high voltage to current delivered by the source is constant.

The processing device of the probe of the invention may comprise either means which make it possible to produce a signal proportional to the difference in the current supplied by the aforesaid two ionization cells or means which make it possible to supply a signal proportional to the ratio of the currents supplied by the said two cells.

Each of the ionization cells advantageously consists of a cylindrical tube of electrically conductive material in the axis of which there is arranged a source electrode consisting of a conductive emission wire supported by suitable insulating means.

In another embodiment of the invention, the electric ionization probe comprises a high voltage supply and an ionization cell comprising a substantially flat electrode connected to the high voltage supply and to a second electrode which is tapered to a point and arranged perpendicular to the flat electrode spaced from the latter so as to constitute a spark gap cell which is arranged in the path of the gases to be analyzed.

It will be noted that the electrode which is tapered to point shape can advantageously be made in the form of a very thin wire whose end is arranged at a certain distance from the opposite substantially flat electrode. The probe of the invention furthermore comprises a processing device which picks up the current appearing on the tapered pointed electrode.

In the event that the probe of the invention is intended to measure the concentration of oxygen in the gases coming from a chemical combustion, the flat electrode is preferably supplied with a positive high voltage. Furthermore this high voltage is preferably not much greater than the initial ionization potential of the oxygen.

In the case of gases coming from a chemical combustion the gaseous mixture generally comprises a large proportion of water whose initial ionization potential is slightly greater than that of oxygen but nevertheless very close to the latter. It has been found that when the probe of the invention was fed in the manner that the flat electrode is positive and the point negative, the electrons emitted pass over a smaller distance so that there was practically no longer any risk of ionizing the molecules of water. The result of the measurement is therefore more precise.

The present invention will be better understood by means of the detailed description of a few embodiments, given by way of illustration and not of limitation, shown in the accompanying drawings in which.

Figure 1:
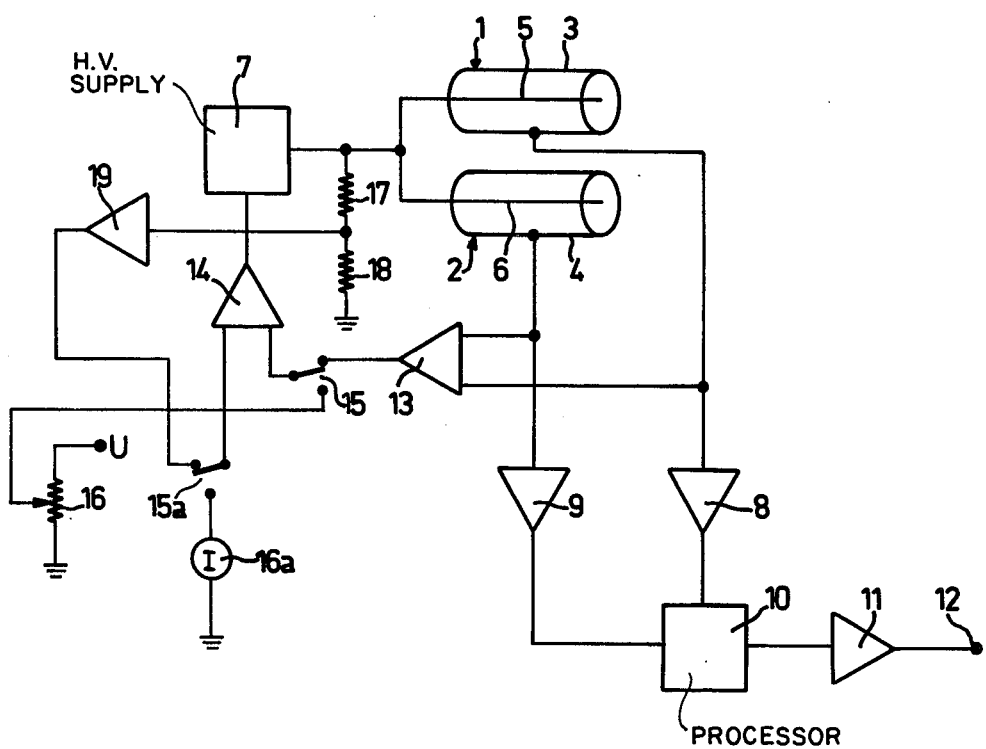
FIG. 1 is a block diagram of a measurement device in accordance with a first embodiment of the present invention.

As shown in FIG. 1, the measurement device of the invention comprises two identical ionization cells 1 and 2. Each of these two cells comprises a cylindrical tube of electrically conductive material 3, 4 respectively, a respective metal wire 5, 6 being arranged in the axis of each tube and insulated from the corresponding electrically conductive tube.

The two wires 5, 6 are connected to each other as well as to a high voltage supply device 7. The high voltage supplied by the supply device 7 is regulated so as to produce a continuous corona discharge between each electrically conductive wire 5,6 and the corresponding tube 3, 4.

Each cylindrical tube 3, 4 is connected, via a respective amplifier 8,9, to an input of a processing device 10 intended to process the ionization currents picked up by the cells 1 and 2. The processing device 10 may establish either the difference between the currents picked up by the cells 1 and 2 or the ratio of these two currents. For this purpose, the processing device 10 comprising, in known manner, one or more operational amplifiers. The processing device 10 is connected, via an amplifier 11, to an output terminal 12 on which there is picked up a signal representing the result of the measurement.

The cylindrical tubes 3, 4 of the probes 1 and 2 are on the other hand each connected to an input of a summing amplifier 13 whose output is connected to one of the fixed contacts of switch 15 whose other fixed contact is connected to the slide of a potentiomer 16 which is fed by a stabilized voltage U. The movable contact of switch 15 is connected to one of the inputs of a comparator amplifier 14 whose other input is connected to the movable contact of a reversing switch 15a one of the stationary contacts of which is connected to a source 16a of reference current and whose other fixed contact, via a resistor divider 17, 18 and an amplifier 19 receives a voltage which is proportional to the high voltage supplied by the supply device 7.

In the position of the switches 15 and 15a shown in FIG. 1, the result of the measurement coming from the amplifier 13 is therefore applied to the supply device 7 via the first input of the comparator-amplifier 14 which furthermore at its second input receives a low voltage which is proportional to the high voltage supplied by the supply device 7, via the amplifier 19 and the switch 15a. There is thus present a regulated system which maintains the ratio $V_{HT}/I_{HT}$ constant whatever the variations of the current measured (in which $V_{HT}$ is the supply voltage of the probes and $I_{HT}$ the current supplied by the device 7).

In the other position of the switch 15 on the other hand the comparator-amplifier 14 receives at its first input a stabilized reference voltage coming from the potentiometer 16. In this case there is a regulated system which maintains the supply voltage of the probes $V_{HT}$ constant. If finally the position of the switch 15a is reversed, connecting the source of reference current 16a to the second input of the comparator-amplifier 14, a regulated system is obtained which maintains the supply current of the probes $I_{HT}$ constant.

In accordance with the preferred embodiment of the invention, the measurement device described above is intended for measuring the percentage of oxygen in the exhaust gases of an internal or external combustion engine. However, the invention is not limited to this field and can be applied in numerous other fields.

In the event that the device of the invention is intended for measuring the percentage of oxygen in the exhaust gases of an internal combustion engine, one of the two cells, for instance the cell 1, is placed in the path of these exhaust gases, preferably in such a manner that the seed of the exhaust gases passing through said cell is low. The cell 2 then serves as reference cell and is to be traversed by the ambient air.

In order to assure proper operation of the measuring device of the invention, it is important that the densities of the gases passing through the two cells 1, 2 be practically equal. Since the density of a gas is equal to the ratio of its pressure to its temperature and since the pressures of the gases passing through the two cells 1, 2 may be practically the same, it is necessary for the temperature of the ambient air passing through the cell 2 to be practically equal to the temperature of the exhaust gases passing through the cell 1. For this purpose, the cell 2 can be arranged in the vicinity of the cell 1 and fed with ambient air through suitable conduits. However, it should be pointed out that the temperatures of the gases passing through the cells 1, 2 need not be absolutely the same, and a difference of 10° C. can in general be tolerated. However, if in certain cases the densities of the gases or their temperatures are very different it is necessary to provide correction circuits (not shown) the connections of which are obvious to the man skilled in the art.

In the preferred embodiment of the invention, the inside diameter of the tubes 3 and 4 is on the order of magnitude of 2 mm and their length is on the order of magnitude of 5 mm. The emission wire 5,6 is of gold-plated tungsten and has a diameter of about 10 to 20 microns. Since the cells 1 and 2 have very small dimensions, it is easy to arrange them, for instance, in an exhaust pipe of an internal combustion engine. However, the dimensions of the cells 1 and 2 may be much greater, the value of the high voltage supplied by the supply device 7 being possibly increased accordingly.

Figure 2:
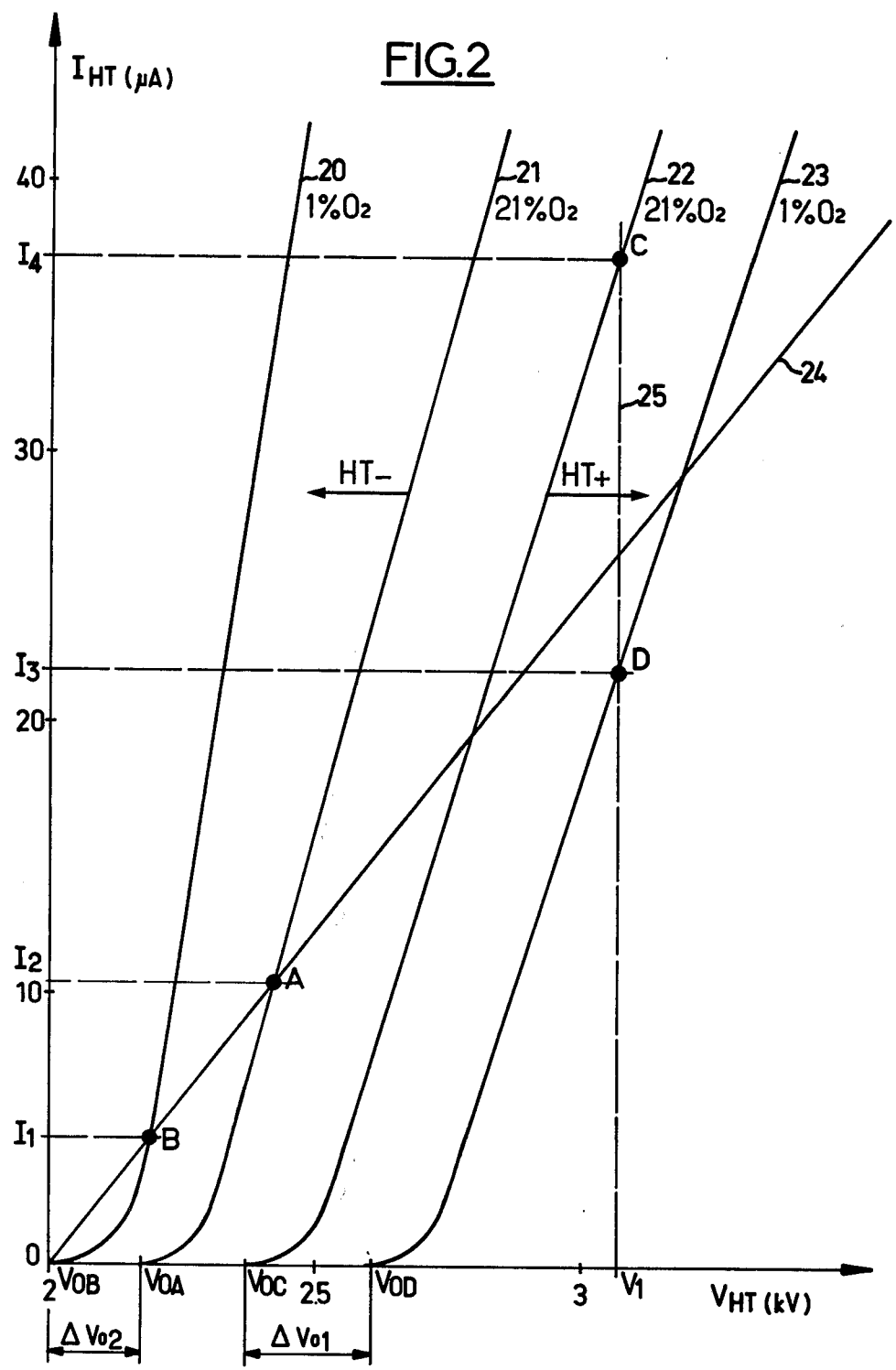
FIGS. 2 to 4 are graphs which make it possible to explain the operation of the measurement device of FIG. 1.

In the graph of FIG. 2 there are shown four characteristic curves, marked 20 to 23, of a cell such as the cells 1 or 2 traversed by gases with different concentrations of oxygen, the curves 21 and 22 corresponding to the case of air of a pressure of 760 mm mercury and a temperature of about 300° K., the curve 21 corresponding to a negative high voltage and the curve 22 to a positive high voltage, the curves 20 and 23 being plotted as described below.

In the graph of FIG. 2 there has also been included a straight line 24 corresponding to a constant $(V_{HT}-V_{OB})/I_{HT}$ $V_{HT}$ and $I_{HT}$ being the voltage and the current supplied by the source 7. It will be noted that the selection of the position of the straight line 24 defined in FIG. 4 by its point of origin $V_{OB}$ is entirely arbitrary and the straight line could be displaced parallel to itself. There has also been included in dashed line the straight line 25 corresponding to a constant value $V_1$ of the high voltage.

Figure 3:
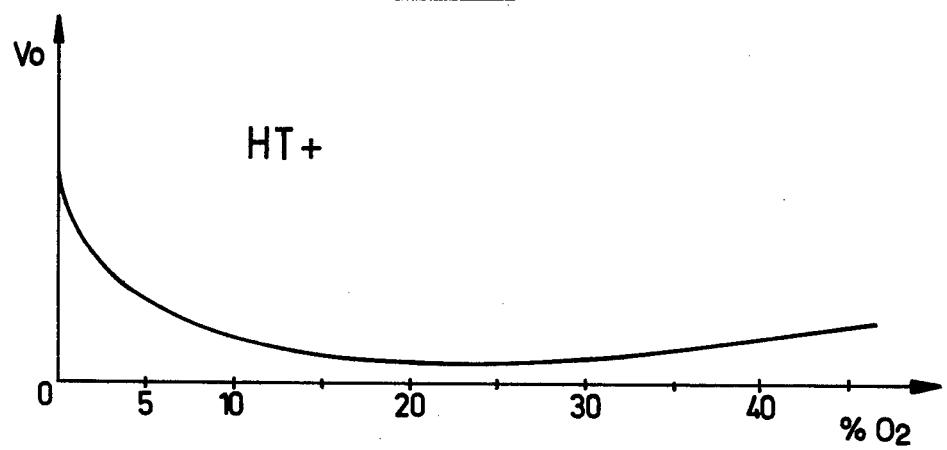
Figure 4:
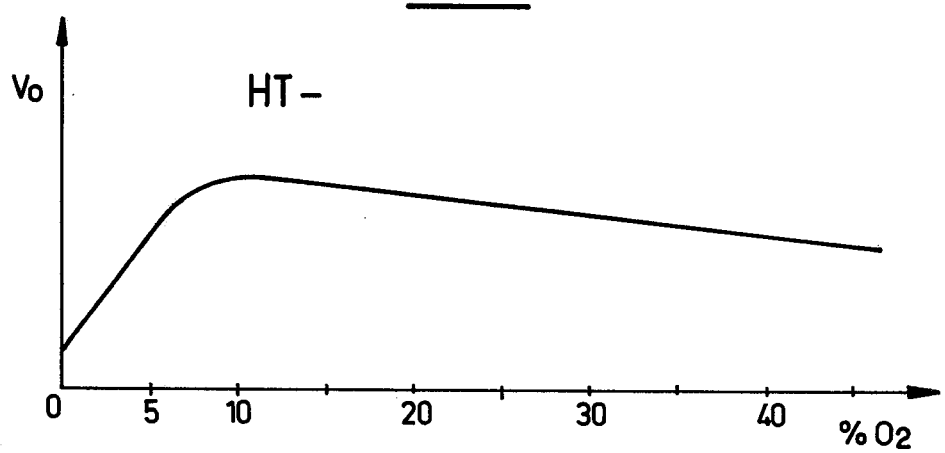

On the other hand, the curves of FIGS. 3 and 4 corresponding respectively to a positive high voltage and a negative high voltage supplied by a source of high voltage to a cell such as that described above show that the value $V_O$ of the initial ionization potential of a cell varies as a function of the proportion of oxygen in the gas passing through said cell. In the case of air at a pressure of 760 mm Hg and about 300° K., the initial ionization potential is about 2400 V for a positive high voltage and about 2000 V for a negative high voltage. For an internal combustion engine operating with a lean mixture, the optimal value of the proportion of oxygen in the exhaust gases should be between 1 and 10% approximately. In the case of a positive high voltage supply, the initial ionization potential $V_O$ of the cell decreases when the proportion of oxygen increases from 0 to 10%, while with a negative high voltage the value of the initial ionization potential increases when the proportion of oxygen increases from 0 to 10%.

Therefore, in order to determine the proportion of oxygen in the exhaust gases, one can enter the values of the initial ionization potential $V_O$ obtained from the curve of FIG. 3 or the curve of FIG. 4 in the graph of FIG. 2 and draw the corresponding curves (20, 23 for instance) of the corresponding ionization current. Thus, by means of the processing device 10 one can supply a signal which is a function of the proportion of oxide in the exhaust gases, the processing device 10 effecting the comparison between the current supplied by the cell placed in the exhaust gases and the current supplied by the reference cell traversed by the ambient air which by definition has a constant oxygen proportion of about 21%, this air being brought to practically the same temperature as the exhaust gases which are to be analyzed.

By means of the graph of FIG. 2 there will now be examined, by way of example the case of a negative high voltage supply and a constant ratio $V_{HT}/I_{HT}$, the first input of the comparator/amplifier 14 being connected to the output of the amplifier 13 and the other input of the amplifier 14 being connected to the output of the amplifier 19 which supplies it with information proportional to the value of the high voltage delivered by the voltage source 7.

Since the proportion of oxygen in the exhaust gases can generally vary within a range of values of between 0 and 10%, it is seen from FIG. 4 that this range is located entirely on the rising portion of the curve shown therein. For the percentage of oxygen in the air (about 21%), there is determined on basis of FIG. 4 the corresponding initial ionization voltage $V_{oA}$. The curve 21 of FIG. 2 was plotted for an ionization cell traversed by air (under the temperature and pressure conditions indicated).

For a given percentage of oxygen of between 0 and 10% approximately, for instance 1%, in the exhaust gases, there is determined, based on the curve of FIG. 4, the corresponding initial ionization potential $V_{oB}$ for which curve 20 of FIG. 2 is obtained practically by horizontal translation of curve 21.

Since the ratio $V_{HT}/I_{HT}$ is maintained constant, the operating point of the cell 1 can only move along the straight line 24 drawn for said constant ratio. Therefore, for the percentage of oxygen of about 21% of ambient air under the conditions indicated, the operating point A of the cell will be at the intersection of curves 21 and 24. For the percentage of oxygen of about 1% for which the curve 20 is obtained, the corresponding operating point of the cell is located at the intersection of curves 20 and 24 and is marked B. Therefore, when the percentage of oxygen increase from the value of about 1% up to the value of 21% the operating point of the cell 1 moves from point B to point A, the corresponding currents detected being $I_1$ and $I_2$.

The processing device 10 compares the current detected by the cell 1 with the current detected by the cell 2 and provides corresponding information which can be used suitably for display or for regulation, for instance.

There will now be explained the case in which the source of power 7 supplies a positive high voltage of constant value, the switch 15 being in the position opposite that shown in FIG. 1, that is to say that the first input of the comparator amplifier 14 receives a constant reference voltage via the potentiometer 16, the switch 15a connecting the second input of the comparator amplifier 14 to the output of the amplifier 19.

For a first percentage of oxygen in the gas measured of about 21% there is obtained curve 22 whose initial ionization potential is $V_{oc}$ (about 2.4 KV) and for a second percentage of oxygen lower than the first (for instance about 1%) one finds from the curve of FIG. 3 the corresponding initial ionization potential $V_{od}$, which is higher than the said first ionization potential $V_{oc}$, it being understood that the percentage of oxygen in all cases remains less than about 25% in the zone within which the characteristic curve of FIG. 3 is constantly decreasing.

Entering the value $V_{od}$ in the graph of FIG. 2, the curve 23 is obtained in the same manner as the curve 20 was obtained. Since, by hypothesis, the high voltage source 7 operates at constant voltage of value $V_1$, the operating points of the cell 1 for the said two percentages of oxygen are located at the intersections of the curves 22 and 23 respectively with the vertical 25 of abscissa $V_1$, the said operating points being marked C and D respectively. To the points C and D there correspond currents $I_4$ and $I_3$ respectively which the processing device 10 transforms into oxygen percentage values. If instead of supplying the cells with constant positive voltage they were fed with constant current, the high voltage being still positive but not regulated (switch 15 in the position shown in FIG. 1 and switch 15a in the opposite position), the measured oxygen percentages being the same as above, the current taken up by the reference cell 2 would decrease and the current taken up by the measurement cell 1 would increase when the percentage of oxygen decreases from 21% to said second percentage since, by hypothesis, the total current supplied by the source 7 remains constant.

It is obvious that if the high voltage supplied by the source 7 is positive, the source 7 can also be regulated in such a manner that the ratio $V_{HT}/I_{HT}$ is constant, and that if the high voltage delivered by the source 7 is negative the source 7 can be regulated in such a manner that it will deliver a current or high voltage of constant value.

The selection of the polarity of the high voltage in this embodiment may depend on several factors; for a negative high voltage the initial ionization potential is generally less than that corresponding to a positive high voltage and in certain cases the difference in supply high voltage may be about 1000 volts, which may offer advantages. However, with a negative high voltage there is still a doubt when the proportion of oxygen exceeds about 10%; to such a proportion of more than about 10% there corresponds the same ionization potential as to a proportion which is less than 10% due to the fact that the curve of FIG. 4 passes through a maximum and it is then necessary to provide a device to remove the doubt.

Likewise, it can be noted from FIG. 2 that, depending on the selection of operation at constant $V_{BT}/I_{HT}$, $V_{HT}$ or $I_{HT}$, the difference in amplitude of the signal received at the output 12 for a given difference in percentage of oxygen (that is to say the amplification coefficient of the measurement device) is greater or less, and the optimal system will be selected for each particular case.

Figure 5:
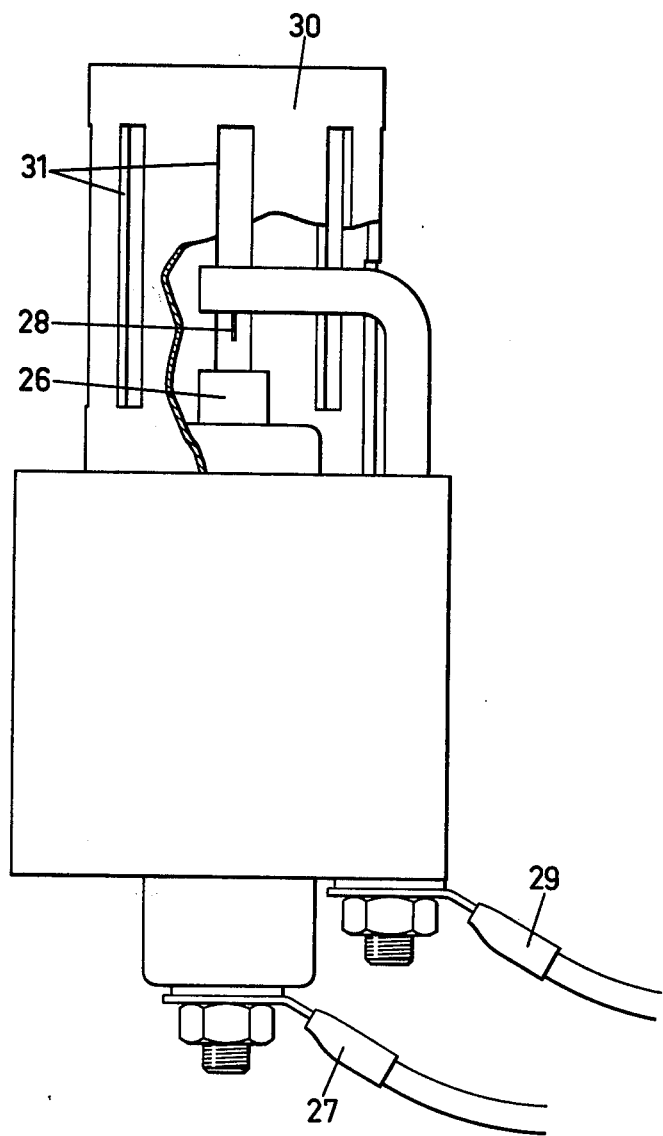
FIG. 5 shows diagrammatically a second embodiment of a probe in accordance with the present invention.

In the embodiment shown diagrammatically in FIG. 5, the probe of the invention, which is placed in the path of the gases to be analyzed, comprises a single ionization cell of the spark-gap type provided with a substantially flat electrode 26 which is brought to the positive potential of a supply high voltage connected to the electrode 26 by the feed wire 27. Opposite the flat surface of the electrode 26 at a distance of a few millimeters from it there is arranged a grounded pointed electrode 28 at negative potential by the electric connection 29. It will be noted that it is important for the flat electrode 26 which is at the positive high voltage potential to have a configuration which is without rough spots. The point-shaped electrode 28 which is arranged perpendicular to the flat surface of the electrode 26 may be made of material which is resistant to high temperature, for instance tungsten. The electrode 28 can advantageously be developed in the form of a single wire of very small diameter arranged perpendicular to the electrode 26 and at a distance of a few millimeters from it.

The arrangement of these electrodes in the form of the ionization cell shown in FIG. 5 can, in order to withstand the high temperatures of the combustion gases to be analyzed, be advantageously contained in a support similar to that of a sparkplug for an internal combustion engine. A metal protective cover 30 having lateral slits 31 which permit the passage of the gases to be analyzed preferably covers the region of the two electrodes 26 and 28 in order to avoid possible disturbances in the measurement due to the speeds of flow or possible solid particles present in suspension in the gaseous mixture to be analyzed.

The processing of the electric signal supplied by the spark-gap ionization cell of FIG. 5 can be effected in any suitable manner. Thus one can measure the average value of the current appearing on the pointed electrode 28. One can also measure the frequency of the electric discharges of the ionization cell. The variations in frequency can be measured by a digital counter with respect to a time reference and provide a measure of the oxygen content present in digital form.

Figure 6:
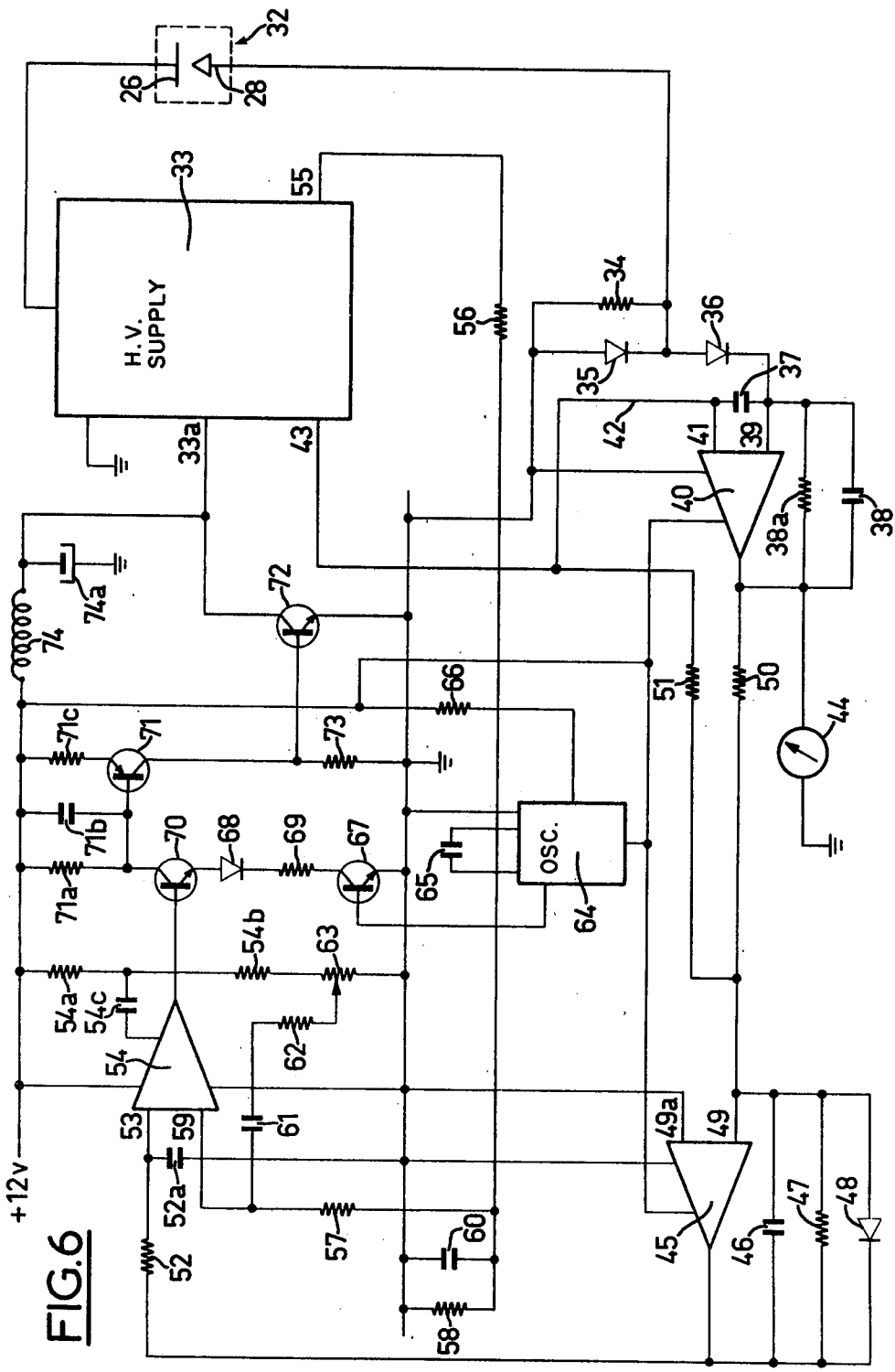
FIG. 6 is a first schematic diagram of a probe in accordance with the invention in which the measurement is effected by maintaining $V_{HT}/I_{HT}$ constant.

FIG. 6 shows, by way of example, an electric circuit which could be used in a probe employing an ionization cell such as that shown in FIG. 5 in which the processing of the signals is effected by detection of the average value of the current, the high voltage supply being regulated in such a manner that the ratio $V_{HT}/I_{HT}$ is maintained constant (straight line 24 in FIG. 2).

In this figure there is found the ionization cell 32 of the spark-gap type such as shown in FIG. 5 in more detail. The flat electrode 26 is connected to the high voltage supply 33. The pointed electrode 28 delivers a pulsating current which results in the appearance at the terminals of the resistor 34 of a voltage which after having been suitably rectified by the diodes 35 and 36 and filtered by the capacitors 37 and 38, is applied to one of the inputs 39 of the amplifier 40 whose gain is fixed by the negative feedback resistor 38a. The amplifier 40 furthermore at its second input 41 receives via the connection 42, a continuous voltage which is proportional to the supply high voltage coming from the output 43 of the supply 33.

The galvanometer 44 located at the output of the amplifier 40 makes it possible to measure the average value of the current appearing on the ionization cell, which average value is proportional to the oxygen concentration sought.

The amplifier 45 which is connected as integrator by means of the capacitor 46 and the negative feedback resistor 47, suitably protected by the diode 48, receives at its first input 49 a voltage proportional to the ratio $V_{HT}/I_{HT}$ via the voltage divider formed of the resistor 50 connected to the output of the amplifier 40 and the resistor 51 connected to the output 43 of the high voltage supply 33. The second input 49a of the amplifier 45 is grounded.

The continuous voltage obtained from the integrator amplifier 45 is applied via the resistor 52 to the input 53 of the error amplifier 54, possible parasitic disturbances being filtered out by the capacitor 52a.

The high voltage coming from the output 55 of the high voltage supply 33 is applied via the voltage divider formed of the resistors 56, 57 and 58 to the second input 59 of the error amplifier 54, the capacitor 60 serving as filter. The capacitor 61, the series resistor 62 and the potentiometer 63 are connected between the input 59 of the amplifier 54 and the supply of the entire circuit and make it possible to regulate the rapidity of response of the regulation loop.

The integrated circuit 64 connected via the capacitor 65 and the resistor 66 constitutes an oscillatory circuit which delivers pulses to the NPN transistor 67 acting as a switch, whose collector is connected by the diode 68 and the resistor 69 to the emitter of the NPN transistor 70. The transistor 70 is connected by its base to the output of the error amplifier 54 and delivers via its collector to the base of the PNP transistor 71 current pulses which are modulated in amplitude by the voltage coming from the error amplifier 54. It will be noted that the latter is connected via the resistors 54a and 54b and the capacitor 54c.

The transistor 71 which is connected in conventional manner via the resistor 71a and the capacitor 71b which are connected to its base in parallel as well as the resistor 71c which is connected to its emitter, delivers at its collector a current which feeds the base of the NPN power transistor 72 via the grounded resistor 73. The pulses coming from the collector of the transistor 72 acting as current generator are applied to the input 33a of the high voltage supply 33. It will be noted that the transistor 72 is not operating in saturation and makes it possible to obtain regulation of the high voltage by the modulation in amplitude of the current of the excitation pulse appearing on its collector.

The circuit is completed by a protective self-induction coil 74 and an electrolytic decoupling capacitor 74a, which are connected to the input 33a.

The high voltage supply 33 which is a printed circuit in the example shown, comprises a power transformer (not shown) constituting an oscillatory circuit which is excited by short pulses coming from the transistor 72.

Finally, it is seen that the entire circuit breaks down into a power circuit, a modulation and control circuit and a circuit for the measurement of the high voltage and amplification of the error signal.

The power circuit is formed primarily of the two transistors 71 and 72 and the high voltage supply 33. The modulation and control circuit comprises the oscillator 64 and the transistor 67 and 70. The circuit for the measurement of the high voltage and error amplification comprises the amplifiers 40 and 45 as well as the error amplifier 54. The entire arrangement constitutes a regulating system which makes it possible to maintain the ratio $V_{HT}/I_{HT}$ constant.

Figure 7:
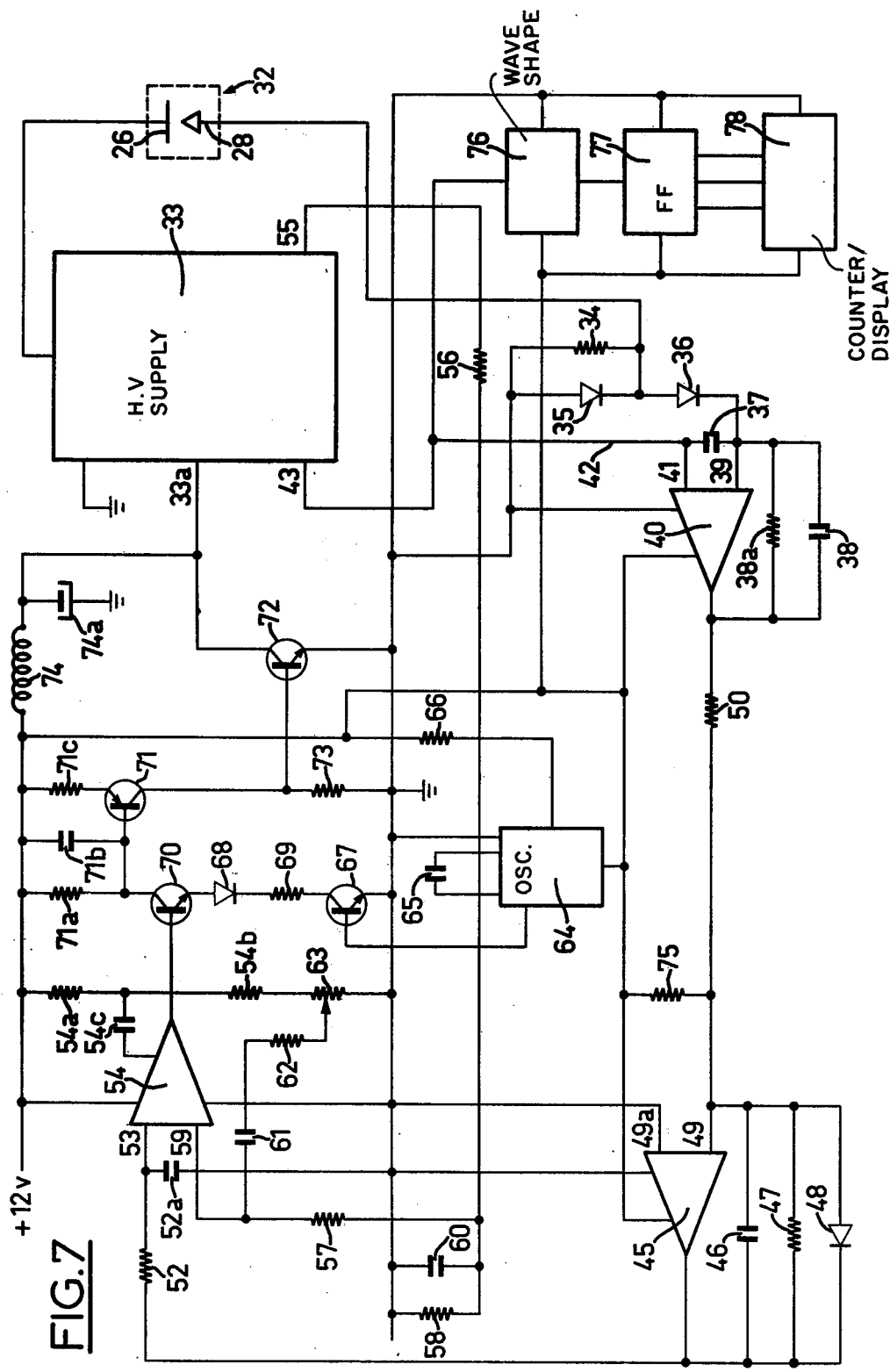
FIG. 7 is a second schematic diagram showing the electric circuit of a probe in accordance with the invention in which the measurement is effected while maintaining the high voltage supply current $I_{HT}$ constant.

The diagram of FIG. 7 in which the same parts bear the same reference numbers as in FIG. 6, shows a regulating system which makes it possible to maintain the current $I_{HT}$ supplied by the high voltage supply constant. In this embodiment, the input 49 of the amplifier 45 no longer receives, as previously, a continuous low voltage signal proportional to the high voltage delivered by the supply 33 and coming from the output 43. In this embodiment, on the contrary, the current is maintained constant by the resistor 75 connected in parallel between the supply voltage of the circuit and the input 49.

The measurement could be effected, as in the embodiment of FIG. 6, by the average value of the current appearing on the pointed electrode 28 of the ionization cell 32, using the same scheme as in FIG. 6. In FIG. 7 there is shown another variant in which, on the other hand, the frequency of the discharges in the ionization cell 32 is measured. In this variant, the low voltage pulses appearing at the output 43 of the high voltage supply 33 are applied directly to a shaping circuit 76 of conventional type which eliminates the parasitic disturbances and then to a flip-flop 77 which permits the counting of the pulses which are then posted on a device 78 which can directly give the percentage of oxygen in the gaseous mixture to be analyzed.

It will be understood, of course, that the measurement of the frequency of the electric discharges in the ionization cell could also be employed in the regulation diagram of FIG. 6.

Due to the apparatus and process of the invention, there is obtained a practically instantaneous measurement of the percentage of oxygen in the exhaust gases, the probes used being practically insensitive to fouling of any kind whatsoever, these probes also being reliable and of inexpensive construction.

As the probes of the invention have very small dimensions they can easily be arranged in the path of the exhaust gases of an automobile engine and the result of the measurement can control a device which regulates the said engine so as to assure it optimum operation, which makes it possible to decrease the pollution caused by its exhaust gases, particularly when idling at which time the air-fuel mixture is lean.

It will be noted that the curves of FIG. 2 have been drawn for gases having a temperature of about 300° K. but it will be easily understood that in actual case of measurement of exhaust gases whose temperature may be far above this value, the curves will be shifted towards the left, the case of the temperature of 300° K. having been selected solely in order to simplify the explanation.

Moreover, it has been assumed in all the above explanations that the ionization was due practically completely to the oxygen, since this gas is the one having the lowest ionization potential among all the gases which can be present in the exhaust gases of a combustion engine. If this should not be so in certain special cases, it would be necessary to vary the voltage and/or the current supplied by the high voltage supply and/or vary the shapes and/or dimensions of one or both measurement cells.

I claim:

1. Apparatus for measuring the oxygen concentration in a gas comprising:
   an ionization-probe comprising an ionization cell having a substantially flat electrode and a pointed electrode disposed substantially perpendicular to said flat electrode at a short distance therefrom;
   a high voltage DC source connected to said flat electrode for providing current to said flat electrode at a voltage sufficiently high to generate successive electric discharges between said electrodes at substantially atmospheric pressure;
   regulating means for holding substantially constant the ratio of the voltage of said DC source to the current in said pointed electrode as oxygen concentration varies; and
   processing circuitry connected to said pointed electrode for measuring the average value of the current flowing therein.

2. Apparatus according to claim 1 further comprising means for measuring the frequency of the discharges in said ionization cell.

3. Apparatus according to claim 2 wherein said means for measuring the frequency of the discharges in said ionization cell includes a counter and a display.

4. Apparatus according to claim 1 wherein said probe has a hood, said hood has openings therein to permit entry of said gas, said hood further providing a protective covering in the region of said electrodes to avoid disturbances in the measurement.

5. Apparatus according to claim 4 wherein said hood is cylindrical and said openings are in the form of slits.

6. A method for measuring the oxygen concentration in a gaseous mixture comprising the steps of:
   passing said gaseous mixture through an ionization cell having a substantially flat electrode and a pointed electrode disposed substantially perpendicular to said flat electrode at a short distance therefrom;
   applying to one of said electrodes a voltage sufficiently high to generate successive electric discharges producing ionization of said gaseous mixture at substantially atmospheric pressure;
   measuring the average value of the current flowing between said electrodes; and
   regulating said applied voltage so as to maintain substantially constant the ratio of said applied voltage to said current flowing between said electrodes as oxygen concentration varies.

7. A method for measuring the oxygen concentration in a gaseous mixture comprising the steps of:
   passing said gaseous mixture through an ionization cell having a substantially flat electrode and a pointed electrode disposed substantially perpendicular to said flat electrode at a short distance therefrom;
   applying to one of said electrodes a voltage sufficiently high to generate successive electric discharges producing ionization of said gaseous mixture at substantially atmospheric pressure;
   measuring the frequency of electric discharges appearing between said electrodes; and
   regulating said applied voltage so as to maintain substantially constant the ratio of said applied voltage to the current flowing between said electrodes as oxygen concentration varies.

8. Apparatus for measuring the oxygen concentration in a gaseous mixture comprising:
   an ionization-probe comprising an ionization cell having a substantially flat electrode and a pointed electrode disposed substantially perpendicular to said flat electrode at a short distance therefrom;
   a high voltage DC source connected to said flat electrode, said high voltage being sufficiently high to automatically generate successive electric discharges between said electrodes at substantially atmospheric pressure;
   regulating means receiving the current flowing in said pointed electrode and comprising integration and amplifier means for regulating the voltage of said source in response of variations of said current as oxygen concentration varies; and
   processing circuitry connected to said pointed electrode for measuring the average value of the current flowing therein.

9. Apparatus of claim 8 further comprising means for measuring the frequency of the discharges in said ionization cell.

10. A method for measuring the oxygen concentration in a gaseous mixture comprising the steps of:
   (a) passing said gaseous mixture through an ionization cell having a substantially flat electrode and a pointed electrode disposed substantially perpendicular to said flat electrode at a short distance therefrom;
(b) applying to one of said electrodes a DC voltage sufficiently high to generate successive electric discharges producing ionization of said gaseous mixture at substantially atmospheric pressure;
(c) measuring the average value of the current flowing in the other electrode as oxygen concentration varies; and
(d) regulating said applied voltage in response to variations of said average value of said current flowing in said other electrodes.

11. A method for measuring the oxygen concentration in a gaseous mixture comprising the steps of:

(a) passing said gaseous mixture through an ionization cell having a substantially flat electrode and a pointed electrode disposed substantially perpendicular to said flat electrode at a short distance therefrom;
(b) applying to one of said electrodes a DC voltage sufficiently high to generate successive electric discharges producing ionization of said gaseous mixture at substantially atmospheric pressure;
(c) regulating said applied voltage in response to variations of the average value of the current flowing in the other of said electrodes as oxygen concentration varies; and
(d) measuring the frequency of electric discharges appearing between said electrodes.

* * * * *